US005741923A

United States Patent [19]

Driver et al.

[11] Patent Number: 5,741,923
[45] Date of Patent: Apr. 21, 1998

[54] ETHYLENICALLY UNSATURATED COMPOUNDS

[75] Inventors: Michael John Driver; Deborah Jane Jackson, both of Surrey, United Kingdom

[73] Assignee: Biocompatibles Limited, Farnham, United Kingdom

[21] Appl. No.: 704,519

[22] PCT Filed: Nov. 23, 1994

[86] PCT No.: PCT/GB94/02571

§ 371 Date: May 23, 1996

§ 102(e) Date: May 23, 1996

[87] PCT Pub. No.: WO95/14702

PCT Pub. Date: Jun. 1, 1995

[30] Foreign Application Priority Data

Nov. 23, 1993 [GB] United Kingdom ............... 9324033

[51] Int. Cl.$^6$ ........................................ C07F 9/09
[52] U.S. Cl. .................... 558/131; 558/100; 558/166; 558/169; 558/170; 558/172; 558/173; 558/174
[58] Field of Search ........................ 558/100, 131

[56] References Cited

FOREIGN PATENT DOCUMENTS

| | | | |
|---|---|---|---|
| 92-07885 | 5/1992 | European Pat. Off. | C08F 212/14 |
| 93/01221 | 1/1993 | European Pat. Off. | C08F 246/00 |
| 93/05081 | 3/1993 | European Pat. Off. | C08F 8/40 |
| 0 580 435 435 | 7/1993 | European Pat. Off. | C07F 9/10 |
| 2 270 887 | 12/1975 | France | A61K 31/685 |
| 60-21599 | 10/1977 | Japan . | |
| 60-184093 | 9/1985 | Japan . | |

OTHER PUBLICATIONS

Chemical Abstracts, vol. 105, No. 12, 22 Sep. 1986, Abstract No. 098087, T. Nakaya et al.
Chemical Abstracts, vol. 100, No. 9,27 Feb. 1984, Abstract No. 068530, T. Nakaya.
Bull. Soc. Chim. de France, 1974, No. 3–4, pp. 667–671. P. Chabrier et al.
Tetrahedron Letters, vol. 32, No. 39, pp. 5291–5294, 1991, Z. Dong et al.
Makromol. Chem., Rapid Commun. vol. 3, pp. 457–459, 1982, T. Umeda et al.
Polymer Journal, vol. 22, No. 5, pp. 355–360, 1990, K. Ishihara et al.
Kobunishi Ronbunshu 1978, vol. 35, No. 7, pp. 423–424.

*Primary Examiner*—Michael G. Ambrose
*Attorney, Agent, or Firm*—Sughrue, Mion, Zinn, Macpeak & Seas, PLLC

[57] ABSTRACT

An improved process for producing ethylenically unsaturated phosphate ester compounds, especially 2-(methacryloyloxyethyl)-2' (trimethylammoniomethyl) phosphate, (HEMA-PC) comprises a two step reaction in the first of which a phospholane reagent is reacted with a hydroxyl containing ethylenically unsaturated starting material, and in the second of which the intermediate formed in the first step is ring opened by reaction with trimethylamine to produce a zwitterionic product. In the process the two steps of the reaction are carried out in the same solvent with substantially no removal or addition of solvent after the first step. The solvent is preferably acetonitrile. The use of pure reagents avoids the production of undesirable by-products. The product is suitable for polymerising, for instance to provide cross-linked hydrogel copolymers used in ophthalmic applications.

18 Claims, No Drawings

ETHYLENICALLY UNSATURATED COMPOUNDS

This application was filed under 35 USC 371 and is based upon PCT International Application No. PCT/GB94/02571, filed Nov. 23, 1994.

The present invention relates to an improved process for producing ethylenically unsaturated phosphate ester compounds. The process is suitable as part of a process for producing polymerisable monomers for use in the production of polymers which mimic cell surfaces. In particular the process involves a two-stage reaction, the successive stages being conducted in the presence of organic solvents. The present invention provides improved products which can be used to form clear polymer products, of particular use for ophthalmological applications, in the manufacture of contact lenses, for example.

The first published route (J.P. Appl. No. 60-21599, Kobunshi Ronbunshu 1978, 35, 7, 423) to 2-(methacryloyloxy ethyl)-2'(trimethylammonium ethyl) phosphate, inner salt (Hema-PC) is illustrated in Scheme I with a trialkylamine has been described by Chabrier and colleagues in -FR-A-2,270,887 and Bul. Soc. Chim. de France (1974) 667–671. The first step is carried out in an organic solvent selected from benzene, ether and tetrahydrofuran. The second step is carried out in an aprotic solvent selected from acetone and acetonitrile. Dong & Butcher in Tetrahedron Letters (1991) 32, 5291–5294 also used the reaction of a hydroxyl group containing compound with a halophospholane, followed by ring opening using trimethylamine to make a synthetic sphingomyelin. The former step was carried out in benzene, with the latter step being carried out in a mixed solvent of benzene and acetonitrile.

An analogous two stage reaction has also been described for producing HEMA-PC, by Nakaya et al, as depicted in scheme 2. The process is described in JP-A-58-154591, 1983 and Makromol. Chem., Rapid Commun., 1982, 3, 457), which involved coupling of 2-hydroxyethylmethacrylate to the chlorophospholane (6) to give intermediate (7) which was trimethylaminated under pressure to give the diester (8).

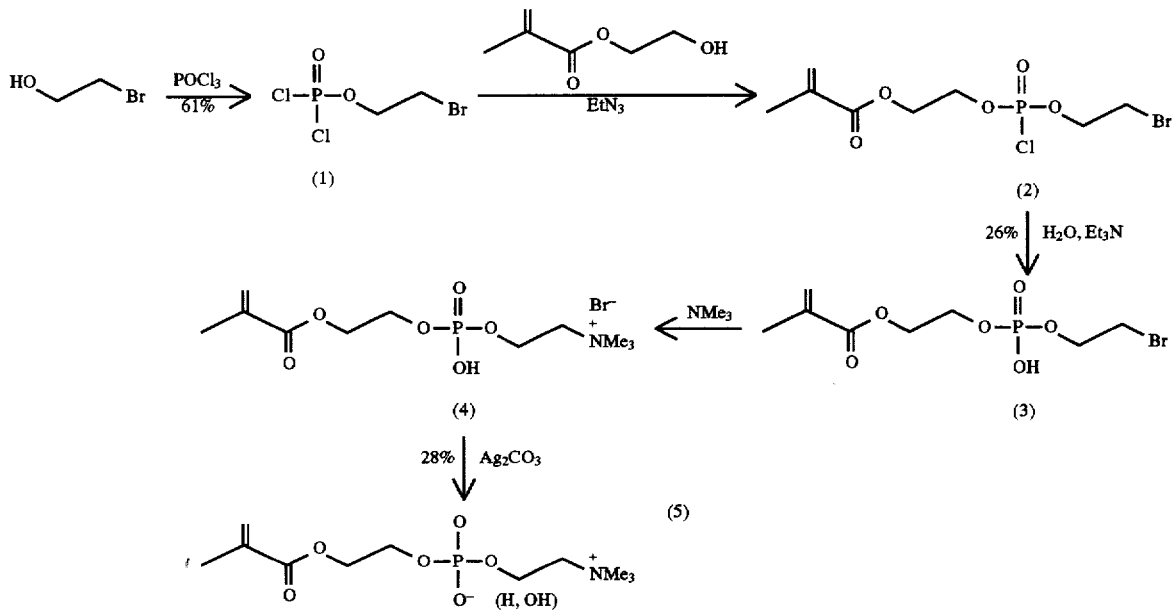

The bromoethyldichlorophosphate (1), obtained from bromoethanol and phosphorus oxychloride, was treated with 2-hydroxyethylmethacrylate to give the phosphate diester chloride (2). Hydrolysis gave the acid analogue (3) which, on reaction with trimethylamine in methanol, gave the phosphorylcholine derivative (4). Conversion to the hydroxide salt (5) was effected using methanolic silver carbonate. The product (5) was isolated using column chromatography on silica-gel and the overall yield was under 5%.

In addition to the low overall yield, purification by column chromatography is inconvenient and expensive, particularly on a larger scale, and the product from this process was isolated in a hydrated form which may not be appropriate for some applications of the product or indeed, for the facile isolation of the product, a point subsequently accepted by the authors (Polymer Journal 1990, 22, 5, 355).

Synthetic processes for producing phosphoryl choline containing lipids, by a two step reaction, in the first step of which a hydroxyl substituted starting material is reacted with a halophospholane, followed by a ring opening reaction Scheme 2

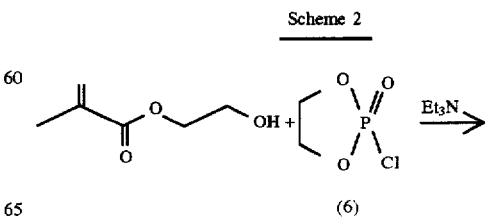

-continued
Scheme 2

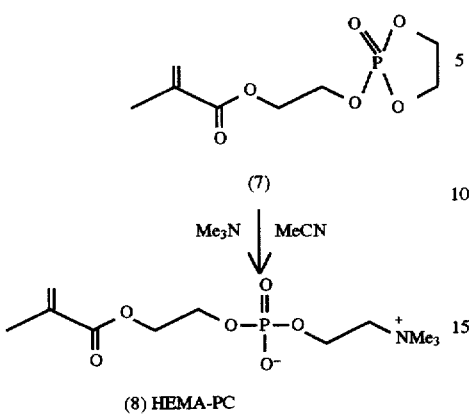

(8) HEMA-PC

For the first stage of the reaction the authors describe the use of ethereal solvents such as diethylether and tetrahydrofuran. Triethylamine hydrochloride, a byproduct of the reaction, precipitated from these solvents and was removed by filtration to give a solution of the phospholane (7). The solvent was then removed by distillation and the residual material dissolved in acetonitrile and heated with trimethylamine to give the product (8) after concentration. Precipitation of chloroform solution of (8) from acetone was the described means of purification. This basic chemical process is described in our earlier publication no. WO-A-92-07885.

We have now found that the product (8), prepared and purified in this way, may not be of the desired purity for certain applications, such as the production of co-polymers intended for fabricating or coating medical devices, for example. In particular, it may not be suitable for use in ophthalmological applications, in the manufacture of contact lenses, for example. The presence of residual reagents or byproducts may have adverse toxicological implications, for example, and the presence of insoluble impurities may have adverse effects on the properties of ophthalmic devices, for example, their light transmission or expansion properties. We have discovered that side-products are formed during the preparation and isolation of the Hema-phospholane derivative (7) as a result of the labile nature of the compound itself and because of the presence of impurities in the chlorophospholane (6) which are not easily discerned. We have also found that the process sometimes fails to give any appreciable amount of product (8) during scaled-up experiments. Furthermore in the process described, in the final step of the reaction a 5-fold excess of trimethylamine is used, hence requiring the use of a pressurised reactor system. It would be desirable to avoid the necessity for the use of such a system. We have now devised a new process to overcome these problems.

A new process according to the present invention comprises:

i) a first stage in which an ethylenically unsaturated compound of the formula I

Y—B—OH    I wherein B is a straight or branched alkylene, oxaalkylene or oligo-oxaalkylene chain, Y is an ethylenically unsaturated polymerisable group selected from

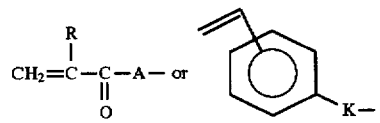

wherein:

R is hydrogen or a $C_1$-$C_4$ alkyl group;

A is —O— or —$NR^1$— wherein $R^1$ is hydrogen or a $C_1$-$C_4$ alkyl group or $R^1$ is a —B—X where B and X are as defined above.

K is a group —$(CH_2)_pOC(O)C$—, —$(CH_2)_pC(O)O$—, —$(CH_2)_pOC(O)O$—, —$(CH_2)_pNR^2$—, —$(CH_2)_pNR^2C(O)$—, —$(CH_2)_pC(O)NR^2$—, —$(CH_2)_pNR^2C(O)$—, —$(CH_2)_pOC(O)NR^2$—, —$(CH_2)_pNR^2C(O)NR^2$— (in which the groups $R^2$ are the same or different), —$(CH_2)_pO$—, —$(CH_2)_pSO_3$—, or a valence bond, and p is from 1 to 12 and $R^2$ is hydrogen or a $C_1$-$C_4$ alkyl group is reacted with a phospholane reagent II

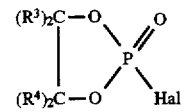

in which each $R^3$ is the same or different and is H or $C_{1-4}$ alkyl, each $R^4$ is the same or different and is H or $C_{1-4}$ alkyl, Hal is halogen atom, to form a diester product compound of the formula III and hydrogen halide by-product

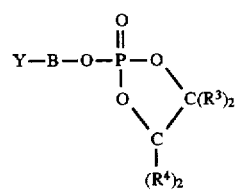

in which Y, B $R^3$ and $R^4$ are as defined previously, the reaction being carried out in the presence of a first solvent in which the ethylenically unsaturated reagent and the phospholane reagent are soluble, the hydrogen halide by-product is removed from the product mixture, and ii) a second stage in which the diester compound III is reacted in the presence of a second solvent, characterised in that the second solvent includes the first solvent and the product mixture from the first stage comprising the compound III and the solvent is used directly in the second stage without isolation of the compound III and substantially without any removal of the first solvent from the product mixture.

Preferred ethylenically unsaturated compounds are those of general formula IA or IB

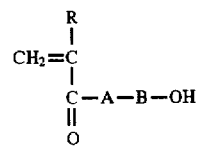

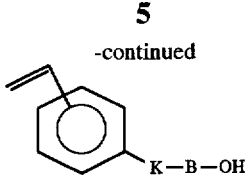

IB where R, A, B and K are as defined with reference to formula (I). Compounds IA are preferred.

Preferably R is hydrogen, methyl, or ethyl, more preferably methyl, so that the monomer of formula IA is an acrylic acid, methacrylic acid or methacrylic acid derivative.

In the compounds of formula IB K may be a valence bond and B a group, K may be a group and B a valence bond, both K and B may be groups or K and B may together be a valence bond. Preferably B is a group where K is a valence bond. Where K is a group then preferably p is from 1 to 6, more preferably 1, 2 or 3 and most preferably p is 1. When K is a group —(CH$_2$)pNR$^2$—, —(CH$_2$)pNR$^2$C(O)—, —(CH$_2$)pC(O)NR$^2$—, —(CH$_2$)pNR$^2$C(O)O—, —(CH$_2$)p OCNR$^2$—, or —(CH$_2$)pNR$^2$C(O)NR$^2$— then R$^2$ is preferably hydrogen, methyl or ethyl, more preferably hydrogen.

Preferably B is:

an alkylene group of formula —(CR$^3_2$)a—, wherein the groups —(CR$^3_2$)— are the same or different, and in each group —(CR$^3_2$)— the groups R$^3$ are the same or different and each group R$^3$ is hydrogen or C$_{1-4}$ alkyl, preferably hydrogen, and a is from 1 to 12, preferably 1 to 6;

an oxaalkylene group such as alkoxyalkyl having 1 to 6 carbon atoms in each alkyl moiety, more preferably —CH$_2$O (CH$_2$)$_4$—;

an oligo-oxaalkylene group of formula —[(CR$^4_2$)bO]c (CR$^4_2$)b— where the groups —(CR$^4_2$)— are the same or different and in each group —(CR$^4_2$)— the groups R$^4$ are the same or different and each group R$^4$ is hydrogen or C$_{1-4}$ alkyl, preferably hydrogen, and b is 2 or 3 and c is from 2 to 11, preferably 2 to 5;

or a valence bond but only if Y contains a terminal carbon atom.

Preferred groups B include a valence bond and alkylene, oxaalkylene and oligo-oxaalkylene groups of up to 12 carbon atoms. B is most preferably a group —(CH$_2$)$_a$,— in which a' is 2 to 4.

In the process of the present invention the hydrogen halide by-product of the first stage is preferably removed by reaction with an organic base, preferably a trialkylamine, to form a hydrogen halide salt of the trialkylamine which precipitates out of the product mixture as it is formed. The hydrogen halide salt may be removed, for instance, by filtration.

Although a small amount of the first solvent may be removed with the hydrogen halide salt after the first step, there is preferably no further removal of solvent prior to the second step.

In some instances it may be desirable to add additional solvent to the solution of compound III prior to the second step. For instance an additional aliqnot of the same solvent may be added or of another compatible solvent type. Usually, however no further addition of solvent is required for the second step.

In the process of the present invention, in the phospholane reagent II, R$^3$ and R$^4$ are preferably each hydrogen. Preferably the halogen atom in compound II is chlorine although other halides may be used. Where the hydrogen halide by-product is removed by reaction with a trialkylamine, that compound is preferably triethylamine.

The preferred phospholane starting material is a commercially available compound. We have discovered that the purity of the compound is of great significance to the process as a whole. If impure phospholane is used, the intermediate diester compound may be unstable, and may prematurely polymerise or, in some instances, may be coloured and thus unsuitable for ophthalmological end uses, or may result in an end product having an unpredictable rate of polymerisation. We believe that impurities in the phospholane starting material which may adversely affect the reaction may be due to contact of the compound with moisture, for instance during storage. The inventors have found that the $^{31}$P nuclear magnetic resonance spectrophotometry is the most appropriate method of analysis for this material, since this can identify polyphosphate species which may result from moisture contact.

In the course of their investigations, the present inventors have found that the intermediate product of the formula III reacts rapidly (in less than 10 minutes) with water at room temperature to form a number of products. Where the group Y B is the residue of a 2-hydroxyethyl methacrylate compound, the by-products of this side reaction include 2-hydroxyethyl methacrylate and the ring opened hydroxyethyl phosphate diester. This compound, it is believed, may result in unwanted polymerisation being initiated, for instance via the phospholane ring of the compound of the formula III.

In the process the side reactions such as those described above are minimised by utilising as a starting material a phospholane reagent of the formula II having a purity by $^{31}$P NMR of at least 90%, more preferably at least 95%, for instance at least 99%. By this we mean that the $^{31}$P NMR trace consists primarily of a single peak, and has only low or insignificant amounts of material with peaks at higher and lower ppm values.

In order to minimise the possibility of moisture contact with the phospholane reagent of the formula II or the diester intermediate of the formula III, the moisture content of the solvent must be kept to minimum. The water content of the solvent, for instance should preferably be less than 0.1% by weight, more preferably less than 0.05% by weight, and most preferably less than 0.01% by weight.

The present inventors have further determined that the diester intermediate of the formula III is thermally unstable. In the conventional process in which different solvents are used in the first and second stages the intermediate III must be recovered from the first solvent. In those processes the recovery is by rotary evaporator. However the inventors have found that the intermediate sometimes undergoes a "run away" reaction leading to complete gelation (by polymerisation of the ethylenically unsaturated groups and/or phosphate groups) and total loss of the final product. This is a particular problem when the reaction is scaled from laboratory to pilot plant scale. Even partial gelation results in insoluble impurities, which are difficult to remove and which contaminate the product leading to non-homogeneous products. The avoidance of this intermediate recovery step avoids exposure of the intermediate to heat, especially when it is in highly concentrated form. Also the product has lower impurity levels and is found to be easier to recover from the product mixture of the second stage.

The process of the present invention is of particular value where the second stage of the process comprises the ring opening amination reaction in which the compound of the formula III is reacted with a trialkylamine (NR$_3^5$) in the said solvent to form a compound of the formula IV

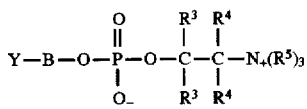

$$Y-B-O-\underset{\underset{O_-}{\|}}{\overset{O}{P}}-O-\underset{\underset{R^3}{|}}{\overset{R^3}{C}}-\underset{\underset{R^4}{|}}{\overset{R^4}{C}}-N_+(R^5)_3 \qquad IV$$

in which each group $R^5$ is a $C_{1-24}$-alkyl group and Y, B, $R^3$ and $R^4$ are each as defined above.

The groups $R^5$ may be the same or different and may be $C_{1-24}$—, preferably $C_{1-12}$-alkyl, preferably lower alkyl, more preferably at least two of the groups $R^5$ being methyl.

The compound IV is a polymerisable compound, that is the ethylenically unsaturated group is capable of undergoing radical initiated addition polymerisation, usually in the presence of ethylenically unsaturated copolymerisable comonomers.

In the second stage of the process, the trialkylamine, which is preferably trimethylamine, is generally used in an excess. It is unnecessary to use an excess of greater than 3 or 2-fold and, where the amine is gaseous, lower amounts are preferred to avoid the necessity of employing pressurised reactor systems. Approximately 1.5-fold excess (that is 1.5 times the stoichiometric amount for reaction with the actual or theoretical amount of the compound III) is found to be convenient.

In the process of the present invention the use of a nitrile solvent in the first stage provides improvements over the prior art utilising the ethereal solvents for that stage for a number of reasons. Firstly, diethyl ether and tetrahydrofuran, two examples of ethereal solvents described in the prior art, are known to form peroxides which, in addition to being potentially explosive, may also promote the hydroperoxidation of the diester intermediate or of the final product. Both those materials may become unstable (for instance may prematurely polymerise) and/or may increase the rate of reaction during copolymerisations, for instance by acting as initiators. Furthermore the nitriles tend to be less hazardous to use and cheaper than the ethereal solvents. Peroxide formation in acetonitrile does not take place, so that the intermediate diester is relatively stable.

In the present process the solvent is preferably a nitrile derivative of a $C_{1-6}$-carboxylic acid. The most readily available suitable solvent is acetonitrile. The present inventors have discovered that the use of acetonitrile, which has been used in prior art process in this second stage, can also be used for the first stage, provided that the relatively pure phospholane reagent II as defined above is used. Otherwise the reaction gives side reactions.

The zwitterionic product of the formula IV is generally recovered from the final product mixture as a solid. The present inventors have discovered that the second stage of the reaction tends to take a place at a rate such that the crystals of the zwitterionic products which are formed are very small. This leads to difficulties in separating them from the product mixture, in particular where the separation involves a filtration step. During a filtration step it is difficult for the filter cake of product to be protected from contact with air and moisture, which could otherwise become absorbed into the product to contaminate it and, possibly, to cause side reactions. The inventors have discovered that these difficulties may be minimised by subjecting the product mixture of the second stage to a special recovery procedure.

In the recovery procedure, it is preferred for the product mixture to be heated to (or maintained at) a temperature at which all of the product zwitterionic compounds of the formula IV is in solution in the solvent, and then allowed to cool, preferably in a sealed vessel, or in a vessel which has been purged with inert gas, for a period of at least one hour, and preferably 2–16 hours, to reach ambient temperature and subsequently cooled further to a temperature in the range −20° to −5° C., preferably around −5° C., at which it is stored for a period of at least 1 hour, for instance in the range 1–24 hours, for instance around 16 hours. The rate of cooling from the temperature at which the zwitterionic product is fully dissolved, which is for instance above 60° C., for instance 70°–80° C., to the final low temperature, is preferably on average at least 10° C. per hour, more preferably at least 15° C. per hour. Subsequently the solid is recovered from the product suspension by filtration, preferably after the mixture is allowed to warm to ambient temperature.

It is preferred for the filtration of the final zwitterionic product to be conducted in an inert atmosphere. That is, after all the liquid has passed through the filter cake of product, any gas which passes through the filter cake comprises an inert atmosphere. Preferably the gas has a moisture content of less than 100 ppm, more preferably less than 10 ppm, for instance less than 1 ppm.

The filter cake is preferably subsequently washed using a dry non-solvent liquid. For instance cold acetonitrile and/or ethyl acetate, each having moisture content of less than 0.1%, more preferably less than 0.01%, may be used to wash the solid.

The solid may subsequently be purified by further recrystallisations, for instance from dry acetonitrile (or other solvent used as the solvent) under similar conditions to the initial recovery of zwitterionic product from the product mixture. Preferably the solution of zwitterionic product in the solvent of the product mixture or of the solution from which the product is to be recrystallised, is subjected to a filtration stage whilst hot, to remove insoluble impurities or by-products from the product. By using the cooling procedure described for the present process larger size crystals of product are produced and this eases the filtration step and minimises the exposure of the solid to potentially moisture containing gas.

Where the present invention uses 2-hydroxyethyl methacrylate as the ethylenically unsaturated starting material I, suitable reaction conditions are as follows.

2-Hydroxyethyl methacrylate is mixed with a suitable non-nucleophilic organic base such as a trialkylamine, preferably triethylamine, in dry acetonitrile and cooled to a temperature between −70° C. and 0°, preferably −10°–5° C. under an inert atmosphere, dry nitrogen for example, and then treated with a solution of the compound II, preferably 2-chloro-2-oxo-1,3,2-dioxaphospholane, in dry acetonitrile drop-wise at a rate such that the temperature of the reaction does not rise above −5° C.–0° C. The reaction mixture is allowed to warm to 0°–5° C., after the addition and stirred for 0.2–3 hours, preferably 1 hour. The precipitate of triethylamine hydrochloride is removed by filtration under an inert atmosphere, for example, by pumping the solution containing the intermediate III from the reaction vessel using a peristaltic pump and a filter stick to leave behind the precipitate. The acetonitrile solution containing III is transferred directly into the reaction vessel in which the second stage trimethylamination reaction takes place. The ratio of acetonitrile to the intermediate III at this stage is preferably around 6:1 though higher (10:1) or lower (1:1) ratios may be used.

After purging with an inert gas, the solution is heated to 50° C. for 5–24 hours, preferably 12–16 hours, with a mixture of trimethylamine (1–5 equivalents, preferably 1–2 equivalents) in dry acetonitrile.

At the end of this period any excess trimethylamine is then removed by applying a low vacuum and the solution then treated with activated charcoal or other suitable decolourising material, and warmed with stirring for 0.2–2 hours, preferably 0.2–0.5 hours at a temperature of 20°–80° C., preferably 70°–80° C. The mixture is then filtered through a filtering aid such as Celite® or pumped into a crystallising vessel using a peristaltic pump and filter stick, using an in-line filter if desired.

The filtrate is then allowed to cool to ambient temperature in a sealed vessel for 1–24 hours, preferably 3 hours and subsequently stored at –20°—5° C., preferably –5° C. for 1–24 hours, preferably 16 hours.

The mixture is allowed to warm to ambient temperature and is filtered under an inert atmosphere. The solid is washed with dry acetonitrile and dry ethyl acetate. The product is then dried in vacuo to give a white, free flowing solid.

These steps allow the isolation of high purity monomer which may, if desired, be further purified by subsequent recrystallisations from dry acetonitrile under similar conditions to those described above.

Analysis of this material using standard techniques including thin layer chromatography (TLC), high performance liquid chromatography (HPLC), nuclear magnetic resonance (NMR) and elemental microanalysis indicates a high level of purity. Solubility evaluation and colour analysis indicates that the isolated material is particularly suitable for use in ophthalmic applications. For instance the monomer may be reacted, eg polymerised, and used in the processes described in our earlier publications WO-A-9305081, WO-A-9207885 and WO-A-9301221, the disclosures of which are herein incorporated by references.

The invention will be illustrated by the following examples.

EXAMPLE 1

The Preparation of 2-(Methacryloyloxyethyl)-2'-(Trimethyl Ammonium)Ethyl Phosphate, Inner Salt (Hema-PC)

2-Chloro-2-oxo-1,3,2-dioxaphospholane (47.68 g, 0.335 mol) having a purity by $^{31}P$ nmr of more than 95% in dry acetonitrile (100 ml) was added dropwise over 0.5 hours to a stirred solution of 2-hydroxyethylmethacrylate (43.54 g, 0.335 mol) and triethylamine (38.21 g, 0.378 mol) in dry acetonitrile (650 ml) at –10° C. On completion of the addition the stirred reaction mixture was allowed to warm to 0° C. over 1.0 hours, filtered under a nitrogen atmosphere and the precipitated triethylamine hydrochloride washed with dry acetonitrile (50 ml) to give a filtrate comprising a solution of cyclic phospholane in acetonitrile.

$^1$H-NMR (200 MHz) (CDCl$_3$): δ 6.19 (1H, s), 5.61 (1H, m), 4.49–4.34 (8H, complex), 1.96 (3H, S) ppm.

The phospholane solution was added to a chilled solution of trimethylamine (29.56 g, 0.501 mol) in dry acetonitrile (300 ml) and purged with dry nitrogen before heating, with stirring, under a closed solid carbon dioxide/acetone condenser at 50° C. for 16 hours. Excess trimethylamine was removed under vacuum and the solution warmed to 75° C., treated with activated charcoal (3.0 g) stirred for 0.25 hours and then filtered through a pad of Celite® under a nitrogen atmosphere. The filtrate was concentrated (ca. 50 ml of acetonitrile removed) and the product allowed to crystallise out of solution at room temperature over 3 hours. This material was stored at –20° C. for 16 hours then allowed to warm to 20° C.

The crystalline product was filtered under a nitrogen atmosphere, washed successively with cold dry acetonitrile (50 ml) and dry ethyl acetate (50 ml) and dried in vacuo at room temperature. Recrystallisation from dry acetonitrile gave 2-(methylacryloyloxyethyl)-2'-(trimethylammoniomethyl) phosphate, inner salt as a white hygroscopic powder.

EXAMPLE 2

A large scale preparation of 2-(methacryloyloxyethyl)-2'-(trimethylammoniomethyl) phohosphate, inner salt Under a dry nitrogen atmosphere a solution of 2-hydroxyethylmethacrylate (0.42 kg, 3.23 mole) and triethylamine (0.38 kg, 3.76 mole) in dry acetonitrile (3.5 l) was cooled to a temperature in the range –15° C. to –10° C. A solution of 2-chloro-2-oxo-1,3,2-dioxaphospholane (0.48 kg, 3.37 mole) in dry acetonitrile (0.9 l) was then added at such a rate that the temperature did not rise above 0° C. The mixture was then stirred for 2.5 hours at a temperature in the range of –10° C. to 0° C. The precipitated triethylamine hydrochloride was removed by filtration under an inert atmosphere and the solution of coupled intermediate treated with trimethylamine (0.28 kg, 4.75 mole) at 60° C. for 18 hours.

Excess trimethylamine was then removed under vacuum and the solution filtered and allowed to stand at –20° C. for 16 hours. The precipitated solid was filtered under an atmosphere of argon, the filter cake washed with acetonitrile (0.5 l) and then ethyl acetate (1 l). The solid material was then dried in vacuo. The crude product was dissolved in dry acetonitrile (1 g/5 ml), the hot solution filtered and the filtrate allowed to stand at –20° C. for 16 hours. The mixture was allowed to warm to 0° C. and was filtered under an argon atmosphere. The solid was washed with chilled, dry acetonitrile (0.5 l) followed by dry ethylacetate (1 l) and was dried in vacuo to yield the title compound as a white powder. The purity of the material as measured by reverse-phase HPLC was greater than 98%.

We claim:

1. A process comprising the following stages:

i) a first stage in which an ethylenically unsaturated compound of the formula I

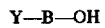

wherein B is selected from the group consisting of alkylene groups of formula —$(CR^3{}_2)_a$—, wherein the groups —$(CR^3{}_2)$— are the same or different, and in each group —$(CR^3{}_2)$— the groups $R^3$ are the same or different and each group $R^3$ is hydrogen or $C_{1-4}$ alkyl and a is from 1 to 12;

alkoxyalkyl groups having 1 to 6 carbon atoms in each alkyl moiety; and oligo-oxaalkylene groups of formula —[$(CR^4{}_2)_b$O]$_c$($CR^4{}_2)_b$— where the groups —$(CR^4{}_2)$— are the same or different and in each group —$(CR^4{}_2)$— the groups $R^4$ are the same or different and each group $R^4$ is hydrogen or $C_{1-4}$ alkyl, b is 2 or 3 and c is from 2 to 11;

Y is an ethylenically unsaturated polymerisable group selected from

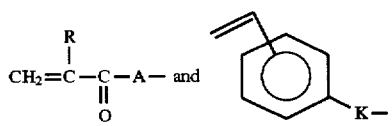

wherein:

R is hydrogen or a $C_1$–$C_4$ alkyl group;

A is —O— or —$NR^1$— wherein $R^1$ is selected from the group consisting of hydrogen, $C_1$–$C_4$ alkyl groups and groups —B—OH;

K is selected from the group consisting of a valence bond and groups —$(CH_2)_pOC(O)C$—, —$(CH_2)_pC(O)O$—, —$(CH_2)_pOC(O)O$—, —$(CH_2)_pNR^2$—, —$(CH_2)_pNR^2C(O)$—, —$(CH_2)_pC(O)NR^2$—, $(CH_2)_pNR^2C(O)$—, —$(CH_2)_pOC(O)NR^2$—, —$(CH_2)_pNR^2C(O)NR^2$— (in which the groups $R^2$ are the same or different), —$(CH_2)_pO$—, and —$(CH_2)_pSO_3$—, in which p is from 1 to 12 and $R^2$ is selected from the group consisting of hydrogen and $C_1$–$C_4$ alkyl groups is reacted with a phospholane reagent II

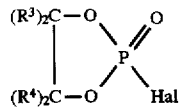

in which each $R^3$ is the same or different and is H or $C_{1-4}$ alkyl, each $R^4$ is the same or different and is H or $C_{1-4}$ alkyl, Hal is halogen atom, to form a diester product compound of the formula III and hydrogen halide by-product

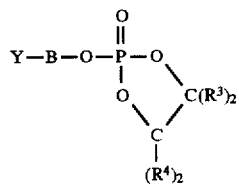

in which Y, B $R^3$ and $R^4$ are as defined previously, the reaction being carried out in the presence of a first solvent which is a nitrile derivative of a $C_{1-6}$-carboxylic acid, in which the ethylenically unsaturated reagent and the phospholane reagent are soluble, the hydrogen halide by-product is removed from the product mixture, and ii) a second stage in which the product mixture from the first stage comprising the compound III and the said first solvent is used directly in the second stage substantially without removal of any of said first solvent, which second stage is a ring opening amination reaction in which the compound of the formula III is reacted with a trialkylamine reagent ($N(R^5)_3$) in the presence of a second solvent which includes substantially all the first solvent to form a zwitterionic compound of the formula IV

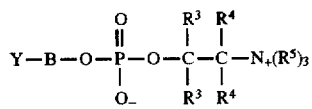

in which each group $R^5$ is the same or different and is a $C_{1-24}$ alkyl group and Y, B, $R^3$ and $R^4$ are each as defined previously.

2. A process according to claim 1 in which the first solvent is acetonitrile.

3. A process according to any preceding claim in which the ethylenically unsaturated compound I is selected from those of general formula IA

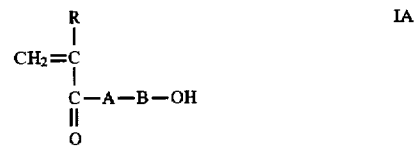

in which R is selected from the group consisting of hydrogen, methyl, and ethyl, A is —O—, and B is as defined in claim 1.

4. A process according to claim 3 wherein R is methyl.

5. A process according to claim 3 wherein B is —$(CR^3_2)_a$— in which each $R^3$ is hydrogen and a is in the range 2 to 4.

6. A process according to claim 1 in which in the phospholane reagent II, $R^3$ and $R^4$ are each hydrogen.

7. A process according to claim 1 in which the phospholane reagent of the formula II has a purity by $^{31}P$ NMR of at least 90%.

8. A process according to claim 7 in which the phospholane reagent has a purity by $^{31}P$ NMR of at least 99%.

9. A process according to claim 1 in which the water content of the first solvent and of the second solvent is less than 0.1% by weight.

10. A process according to claim 9 in which the water content of the first solvent and of the second solvent is less than 0.01% by weight.

11. A process according to claim 1 in which at least 2 of the groups $R^5$ are methyl.

12. A process according to claim 11 in which all of the groups $R^5$ are methyl.

13. A process according to claim 1 in which the trialkylamine reagent is present in the reaction mixture for the second stage in an amount in the range 1 to 2 of the stoichiometric amount for reaction with the compound of the formula III.

14. A process according to claim 1 in which the product mixture of said second stage containing IV is heated to a temperature at which all of the product said zwitterionic compound of the formula IV is in solution in the solvent, and then allowed to cool, for a period of at least 1 hour, to reach ambient temperature and subsequently cooled further to a temperature in the range –20° to –5° C., at which it is stored for a period of at least 1 hour.

15. A process according to claim 14 in which a solution of the zwitterionic compound of formula IV is allowed to cool in a vessel which has been purged with inert gas, for a period of 2–16 hours, to reach ambient temperature and subsequently cooled further to a temperature around –5° C., at which it is stored for a period in the range 1–24 hours.

16. A process according to claim 14 or 15 in which the solid product IV is removed from the product suspension by filtration.

17. A process according to claim 16 in which the filtration is conducted in an inert atmosphere.

18. A process according to claim 17 in which the filtration is conducted in an inert atmosphere such that any gas which passes through the filter cake has a moisture content of less than 1 ppm.

* * * * *